United States Patent
Kramer et al.

(10) Patent No.: US 11,534,419 B2
(45) Date of Patent: *Dec. 27, 2022

(54) N-ACETYL BETA ALANINE METHODS OF USE

(71) Applicant: ThermoLife International, LLC, Phoenix, AZ (US)

(72) Inventors: Ronald Kramer, Phoenix, AZ (US); Alexandros Nikolaidis, Nea Kallikratia (GR)

(73) Assignee: ThermoLife International, LLC, Signal Hill, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/456,637

(22) Filed: Aug. 11, 2014

(65) Prior Publication Data

US 2014/0350108 A1 Nov. 27, 2014

Related U.S. Application Data

(63) Continuation of application No. 13/446,416, filed on Apr. 13, 2012, now Pat. No. 8,802,731.

(60) Provisional application No. 61/475,179, filed on Apr. 13, 2011.

(51) Int. Cl.
*A61K 31/198* (2006.01)
*A61K 31/197* (2006.01)

(52) U.S. Cl.
CPC .......... *A61K 31/198* (2013.01); *A61K 31/197* (2013.01)

(58) Field of Classification Search
CPC ........................... A61K 31/197; A61K 31/198
See application file for complete search history.

(56) References Cited

U.S. PATENT DOCUMENTS

| | | | |
|---|---|---|---|
| 1,916,983 A | 7/1933 | Garnet |
| 2,176,144 A | 10/1939 | Moskowitz |
| 2,553,533 A | 5/1951 | Komarik |
| 3,230,036 A | 1/1966 | Kappelmann |
| 3,552,978 A | 1/1971 | Inklaar |
| 3,886,040 A | 5/1975 | Chibata |
| 3,997,659 A | 12/1976 | Knohl |
| 4,146,611 A | 3/1979 | Ondetti |
| 4,379,177 A | 4/1983 | McCoy |
| 4,687,782 A | 8/1987 | Brantman |
| 4,743,614 A | 5/1988 | Terano |
| 4,871,550 A | 10/1989 | Millman |
| 4,976,960 A | 12/1990 | Grossman |
| 4,996,067 A | 2/1991 | Kobayashi |
| 5,026,071 A | 6/1991 | Miraglia, Jr. |
| 5,026,721 A | 6/1991 | Dudrick |
| 5,242,697 A | 9/1993 | Luca |
| 5,500,436 A | 3/1996 | Schoenafinger |
| 5,543,430 A | 8/1996 | Kaesemeyer |
| 5,576,351 A | 11/1996 | Yoshimura |
| 5,631,031 A | 5/1997 | Meade |
| 5,679,704 A | 10/1997 | Schoenafinger |
| 5,767,160 A | 6/1998 | Kaesemeyer |
| 5,904,924 A | 5/1999 | Gaynor |
| 5,965,596 A | 10/1999 | Harris |
| 6,063,432 A | 5/2000 | Maxwell |
| 6,136,339 A | 10/2000 | Gardiner |
| 6,159,485 A | 12/2000 | Yu |
| 6,172,098 B1 | 1/2001 | Harris |
| 6,277,884 B1 | 8/2001 | De Tejada |
| 6,337,349 B2 | 1/2002 | Scafetta |
| 6,451,341 B1 | 9/2002 | Slaga |
| 6,562,869 B1 | 5/2003 | Hamilton |
| 6,608,109 B2 | 8/2003 | Allen |
| 6,784,209 B1 | 8/2004 | Gardiner |
| 7,235,237 B2 | 6/2007 | Loscalzo |
| 7,777,074 B2 | 8/2010 | Kramer |
| 7,799,782 B2 | 9/2010 | Munson |
| 8,034,836 B2 | 10/2011 | Kramer |
| 8,048,921 B2 | 11/2011 | Kramer |
| 8,178,572 B2 | 5/2012 | Kramer |
| 8,183,288 B2 | 5/2012 | Kramer |
| 8,455,531 B2 | 6/2013 | Kramer |
| 8,466,187 B2 | 6/2013 | Kramer |
| 8,569,368 B2 | 10/2013 | Kramer |
| 8,569,369 B2 | 10/2013 | Kramer |
| 8,703,719 B1 | 4/2014 | Abraham |
| 8,952,045 B1 | 2/2015 | Kramer |
| 8,952,046 B1 | 2/2015 | Kramer |
| 8,957,100 B1 | 2/2015 | Kramer |
| 8,957,101 B1 | 2/2015 | Kramer |
| 9,180,140 B2 | 11/2015 | Lundberg |
| 2001/0002269 A1 | 5/2001 | Zhao |

(Continued)

FOREIGN PATENT DOCUMENTS

| | | |
|---|---|---|
| CN | 1056225 | 11/1991 |
| CN | 1049824 | 3/2000 |

(Continued)

OTHER PUBLICATIONS

Blodgett et al. "Incidence of Hematologic Disease in Patients with Carpal Tunnel Syndrome" JAMA, 1962, 182(7), pp. 814-815.*
Simplico et al. "Prodrus for Amines", Molecules 2008, vol. 13, pp. 519-547.*
Wilson et al., "Beta-Alanine-Bad Ass Supplement", Iron Man Magazine, Oct. 13, 2010.*
Anders et al. "Aminoacylases", 1994, Advances in Pharmacology, vol. 27, pp. 431-448. (Year: 1994).*
Harris et al. "The absorption of orally supplied beta-alanine and its effect on muscle carnosine synthesis in human vastus lateralis" Amino Acids, 2006, vol. 30, pp. 270-289. (Year: 2006).*
Artioli et al., "Role of B-Alanine Supplementation on Muscle Carnosine and Exercise Performance", Medicine & Science in Sports & Exercise, Jun. 2010, vol. 42, No. 6, pp. 1162-1173.

(Continued)

*Primary Examiner* — Kara R McMillian
(74) *Attorney, Agent, or Firm* — Booth Udall Fuller, PLC; Pacer K. Udall

(57) ABSTRACT

Method for preventing paresthesia in a human is disclosed. The method includes administering to the human an effective amount of N-Acetyl Beta Alanine or an N-Acetyl Beta Alanine composition.

7 Claims, No Drawings

(56) References Cited

U.S. PATENT DOCUMENTS

| | | |
|---|---|---|
| 2001/0048952 A1 | 12/2001 | Siskind |
| 2001/0055617 A1 | 12/2001 | Mattern |
| 2001/0056069 A1 | 12/2001 | Klaus |
| 2002/0006532 A1 | 1/2002 | Robin |
| 2002/0065323 A1 | 5/2002 | Crooks |
| 2002/0119933 A1 | 8/2002 | Butler |
| 2002/0147156 A1 | 10/2002 | Petit |
| 2003/0012744 A1 | 1/2003 | Pedersen |
| 2003/0014238 A1 | 1/2003 | Xun |
| 2003/0091615 A1 | 5/2003 | Craig |
| 2003/0097401 A1 | 5/2003 | Bauman |
| 2003/0119888 A1 | 6/2003 | Allen |
| 2003/0139354 A1 | 7/2003 | Buccholz |
| 2004/0006140 A1 | 1/2004 | Kaesemeyer |
| 2004/0057926 A1 | 3/2004 | Ochoa |
| 2004/0087518 A1 | 5/2004 | Verlaan |
| 2004/0097401 A1 | 5/2004 | Datta |
| 2004/0126366 A1 | 7/2004 | Kaddurah-Daouk |
| 2004/0242682 A1 | 12/2004 | Kaesemeyer |
| 2005/0043274 A1 | 2/2005 | Murad |
| 2005/0053673 A1 | 3/2005 | Netke |
| 2005/0171194 A1 | 8/2005 | Yu |
| 2005/0196474 A1 | 9/2005 | Anno |
| 2005/0256192 A1 | 11/2005 | Gardiner |
| 2005/0261257 A1 | 11/2005 | Vermeer |
| 2005/0287210 A1 | 12/2005 | Ron |
| 2005/0288372 A1 | 12/2005 | Ron |
| 2005/0288373 A1 | 12/2005 | Ron |
| 2006/0014238 A1 | 1/2006 | Gholap |
| 2006/0018281 A1 | 1/2006 | Sadot |
| 2006/0029668 A1 | 2/2006 | Ron |
| 2006/0063827 A1 | 3/2006 | Yu et al. |
| 2006/0116328 A1* | 6/2006 | Babizhayev ............ A61P 35/00 514/5.5 |
| 2006/0142382 A1 | 6/2006 | Morimoto |
| 2006/0182815 A1 | 8/2006 | Gladwin |
| 2006/0198899 A1 | 9/2006 | Gardiner |
| 2006/0241181 A1 | 10/2006 | Pola |
| 2006/0275909 A1 | 12/2006 | Spitzer |
| 2007/0105817 A1 | 5/2007 | Page |
| 2007/0141174 A1 | 6/2007 | Cornett |
| 2007/0154569 A1 | 7/2007 | Gladwin |
| 2008/0004218 A1 | 1/2008 | Quay et al. |
| 2008/0026075 A1 | 1/2008 | Kondo |
| 2008/0138448 A1 | 6/2008 | Heuer |
| 2008/0214649 A1* | 9/2008 | Yu ........................ A61K 31/401 514/423 |
| 2008/0233186 A1 | 9/2008 | Romero |
| 2008/0268095 A1 | 10/2008 | Herzog |
| 2009/0076110 A1 | 3/2009 | Kramer |
| 2009/0137670 A1 | 5/2009 | Kramer |
| 2009/0280199 A1 | 11/2009 | Russell |
| 2009/0306208 A1 | 12/2009 | Shimada |
| 2010/0004335 A1 | 1/2010 | Kagami |
| 2010/0047344 A1 | 2/2010 | Lundberg |
| 2010/0092441 A1 | 4/2010 | Lundberg |
| 2010/0172890 A1 | 7/2010 | Gilad |
| 2011/0064712 A1 | 3/2011 | Amato |
| 2011/0123654 A1 | 5/2011 | Jaeger |
| 2012/0220643 A1 | 8/2012 | Kramer |
| 2013/0101704 A1 | 4/2013 | Meehan |
| 2015/0246066 A1 | 9/2015 | Nelson |
| 2018/0133247 A1 | 5/2018 | Green |

FOREIGN PATENT DOCUMENTS

| | | |
|---|---|---|
| CN | 1631539 | 6/2005 |
| CN | 20041009958 | 6/2005 |
| EP | 1336602 | 8/2003 |
| GB | 1089084 A | 11/1967 |
| GB | 2008578 A | 6/1979 |
| GB | 2354441 | 3/2001 |
| KR | 20110015141 A | 2/2011 |
| WO | 9843499 | 10/1998 |
| WO | 0040217 | 7/2000 |
| WO | 0195897 | 12/2001 |
| WO | 03063789 A2 | 8/2003 |
| WO | 2005062713 | 7/2005 |
| WO | 2005115175 | 12/2005 |
| WO | 2005115175 A1 | 12/2005 |
| WO | 2006025286 | 3/2006 |
| WO | 2006124161 | 11/2006 |
| WO | 2007000985 | 1/2007 |
| WO | 2007066642 | 6/2007 |
| WO | 2008009615 A1 | 1/2008 |
| WO | 2008105730 | 9/2008 |
| WO | 2008105731 | 9/2008 |
| WO | 2021188163 | 9/2021 |

OTHER PUBLICATIONS

Glyceryl trinitrate—leaflet print—Patient UK, available at http://www.patient.co.uk/printer.asp?dock=30003883, 2009.

Heart attack—Nitrates & vasodilators—Revolution Health, available at http://www.revolutionhealth.com/conditions/ heart/herat-attack/medication-types/nitrates-vasodilators/.

"Isosorbide dinitrate—leaflet print—Patient UK," available at http://www.patient.co.uk/printer.asp?doc= 30003884, 2011.

"Isosorbide mononitrate—leaflet print—Patient UK," available at http://www.patient.co.uk/printer.asp?doc=30003885, 2008.

"Dietary Nitrate and Nitrite to Increase Nitric Oxide in Patients with Coronary Artery Disease," Clinical Trial available at http://clinicaltrials.gov/ct2/show/NCT00069654, 2010.

"Dymatize Nutritional Supplements, Whey Protein, Bodybuilding & Weight Products", 2013 Dymatize Enterprises LLC, Xpand 2x36 Serving, http://www.dymatize.com/products/nitric-oxide/detail/1166/xpand-2x-36-serving, 2013.

"Heart attack—Nitrates & vasodilators—Revolution health," available at http://www.revolutionhealth.com/conditions/heart/heart-attack/medication-types/nitrates-vasodilators, 2011.

"Nitrates and nitrites (PIM G016)," available at http://www.inchem.org/documents/pims/chemical/pimg016.htm, 2011.

"Nitrates and Nitrites", TEACH Chemical Summary, U.S. EPA, Toxicity and Exposure Assessment for Children's Health, published by the U.S. Environmental Protection Agency on May 22, 2007 (Year: 2007).

"Xpand 2x by Dymatize at Bodybuilding.com—Lowest Price on Xpand 2x!", Advertisement, 2012 BodyBuilding.com, LLC., http://www.bodybuilding.com/store/dymatize/xpand-2x.html, Jun. 8, 2013.

21 C.F.R. (I)(B) §§ 172.160 and 172.170, revised Apr. 1, 2018 (Year: 2018).

A Butler, et al., Medieval Chinese Medicine: The Dunhuang Medical Manuscripts (Chapter 16: A treatment for carenovascular dysfunction in a Dunhuang medical manuscript), Routledge (2005).

Abd El-Gawad et al. AAPS PharmaSciTech, 2017, 18(5):1795-1809.

Abou-Mohamed et al. "Role of L-Arginine in the Vascular Actions and Development of Tolerance to Nitroglycerin", British Journal of Pharmacology (2000) 130, 211-218.

Ahtee et al."Taurine Biological Actions and Clinical Perspectives," J. Nutr. 116:2555-2556 (1986).

Amino Thrust dietary supplement, 2007.

Anderson, K. "Nitrate and Nitrite in Human Nutrition" The Graduate College in the University of Nebraska, Lincoln, Nebraska, 1982.

Aniya et al., "Evaluation of Nitric Oxide Formation from Nitrates in Pig Coronary Arteries," Jpn. J. Pharmacol. 71:101-107 (1996).

Archer, Evidence that ingested nitrate and nitrite are beneficial to health, Journal of food protection, vol. 65, No. 5, pp. 872-875, 2002.

Arenas et al., Muscle & Nerve, 1991, 14:598-604.

Arnold Iron CRE3, 2007.

Atanasova, Plant Siol Environ, 2008, 54(2):66-71.

ATSDR Case Studies in Environmental Medicine Nitrate/Nitrite Toxicity published by the U.S. Department of Health and Human Services on Dec. 5, 2013. ATSDR Case Studies in Environmental Medicine Nitrate/Nitrite Toxicity.

(56) References Cited

OTHER PUBLICATIONS

Avraham et al., "Tyrosine improves appetite cognition and exercise tolerance in activity anorexia," Medicine & Science in Sports & Exercise, 33(12): 2104-2110, 2001.
B. C. Challis, Nutrition and nitrosamine formation, Proceeds of the Nutrition Society, vol. 44, pp. 95-100 (1985).
B. Spiegelhalder, et al., Influence of Dietary Nitrate On Nitrate Content of Human Saliva: Possible Relevance of N-Nitroso Compounds, Fd. Cosmet. Toxicol., vol. 14, pp. 545-548 (1976).
B. Sridhar, et al., "Bis (beta-alanine) Hydrogen Nitrate", Acta Crystallographica Section, 2001, pp. 1004-1006vol. 57.
Bahadur et al., "Crystal and molecular stucture of DL-aspartic acid nitrate monohydrate," Z. Kristallogr. 210: 276-278, 1995.
Bailey et al. "Dietary nitrate supplementation reduces the O2 cost of low-intensity exercise and enhances tolerance to high-intensity exercise in humans", J. Appl. Physiol., 2009, vol. 107, pp. 1144-1155. (Year: 2009).
Baran, "Crystal structure, phase transitions and vibrational spectra of bis(betaine) nitrate," Journal of Molecular Structure, 372: 131-144, 1995.
Barger, G. (1914) The Simpler Natural Bases. In R.H.A. Plimmer& F.G. Hopkins (Eds.) Monographs on Biochemistry (pp. 157-163) Longmans, Green & Co., London.
Barron JT and Parillo JE, "Production of lactic acid and energy metabolism in vascular smooth muscle: effect of dichloroacetate." Am J Physiol. Feb. 1995;268(2 Pt 2):H713-9.
Basheva et al."Role of Betaine as Foam Booster in the Presence of Silicone Oil Drops," Langmuir 16:1000-1013 (2000).
Bauer et al., "Vascular and Hemodynamic Differences between Organic Nitrates and Nitrites," Journal of Pharmacology and Experimental Therapeutics 280:326-331 (1997).
Bauer et al."Photochemical Generation of Nitric Oxide from Nitrocontaining Compounds: Possible Relation to Vascular Photorelaxation Phenomena," Life Science 54(1):PL1-PL4 (1994).
BeetVO2Max—max Nitric Oxide Booster, Amazon.com, 2006.
Beghetti et al."Nitric oxide precursors and congenital cardiac surgery: A randomized controlled trial of oral citrulline. Definition of pulmonary hypertension in Fontan circulation?" J Thorac Cardioasc Surg 132(6):1501-1502 (2006).
Bendahan et al., "Citrulline/malate promotes aerobic energy production in human exercising muscle," Br. J. Sports Med., 36: 282-289, 2002.
Benjamin, Nigel, Nitrates in the Human Diet—good or bad?, Ann. Zootech. vol. 49, pp. 207-216 (2000).
Berge et al., Journal of Pharmarceutical Science, 66(1):1-19, 1977.
Betancourt product: Betancourt Ripped Juice EX2, 2006.
Beverly International advertisement in Dec. 1987 edition of Muscle & Fitness.
Bloomer et al., "Comparison of pre-workout nitric oxide stimulating dietary supplements on skeletal muscle oxygen saturation, blood nitrate/nitrite, lipid peroxidation, and upper body exercise performance in resistance trained men", Journal of the International Society of Sports Nutrition 2010, 7:16, http://www.jissn.com/content/7/1/16.
Bloomer et al."Glycine propionyl-L-carnitine increases plasma nitrate/nitrite in resistance trained men," Journal of the International Society of Sports Nutrition 4(22):1-6 (2007).
Boger, "The Pharmacodynamics of L-Arginine," J. Nutr. 137: 1650S-1655S (2007).
Boguslavskiy. Effect of nitric oxide on the efficiency of oxygen usage by a working skeletal muscle under fatigue, Fiziol. Zhum., vol. 51, No. 1, pp. 33-42 (2005) & Certified Translation.
Borison et al., "Brain 2-phenylethylamine as a major mediator for the central actions of amphetamine and methylphenidate," Life Sci., 17: 1331-1344, Nov. 1975.
Bover-Cid et al., "Biogeneic Amine Accumulation in Ripened Sausages Affected by the Addition of Sodium Sulphite", Meat Science 59 (2001) 391-396, Mar. 20, 2001.
Bryan, N., "Food, Nutrition and the Nitric Oxide Pathway: Biochemistry and Bioactivity" 2010, pp. 59-63.

BSN Volumaize Aretic Blast, on line, sale product, 2014.
Burtscher. The Proonged Intake of L-Arglnine-L-Aspartate Reduces Blood Lactate Accumulation and Oxygen Consumption During Submaximal Exercise, Journal of Sports Science and Medicine, vol. 4, pp. 314-322 (2005).
C. Oldreive, et al., The Mechanisms for Nitration and Nitrotyrosine Formation in vitro and in vivo: Impact of D;et, Free Rad. Res., vol. 35, pp. 215-231 (2001).
CAS Registry No. 89695-59-0 (1984).
Cavassa et al. WO98/43499.
CFIndustries, "Material Safety Data Sheet for Urea Ammonium Nitrate Solution (UAN)," available at www.cfindustries.com/pdf/UANMSDS.pdf Oct. 25, 2006.
Chabot et al., "Characterization of the vasodilator properties of peroxynitrite on rat pulmonary artery: role of poly (adenosine 5'-diphosphoribose synthase," British Journal of Pharmacology 121:485-490 (1997).
Chang et al., "Arginase modulates nitrix oxide production in activated macrophages," Am. J. Physiol., 274: H342-348, 1998,.
Chemical Abstracts Service, "Chemical Abstracts", The American Chemical Society, Liquid Crystals, vol. 104, Jun. 2, 1986.
Colormaker, 2006.
CPG Sec 565.100 FDA Jurisdiction Over Meat and Poultry Products, 2005.
Craig, "Betaine in human nutrition," Am J Clin Nutr, 80:539-549,2004.
Creatine from Wikipedia, 2017.
Creatine nitrate from PubChem, 2017.
Cromwell et al., "The Biosynthesis and Metabolism of Betaines in Plants," 1953 Biochem J., 55: 189-192.
Crooks et al., U. S. Patent Application Publication No. 2002/0065323 A1, published May 30, 2002.
Curtis, J., Dec. 6, 2017, "Nitrate-Free Bacon: Myth or Reality", https://firsthandfoods.com/author/jennifer/, pp. 1-2 (Year: 2017).
D. D. Rees, et al., Role of endothelium-derived nitric oxide in the regulation of blood pressure, Proc. Natl. Acad. Sci. USA, vol. 86, pp. 3375-3378 (May 1989).
Danov et al., "Mixed Solutions of Anionic and Zwitterionic Surfactant (Betaine): Surface Tension Isotherms, Adsoprtion, and Relaxation Kinetics," 2004 Langmuir 20: 5445-5453.
Declaration of James L. Bono Under 37 C.F.R. § 1.132 dated Aug. 27, 2014.
Declaration of Richard Chamberlin Dessaignes, Comptes Rendus 1854 Under 37 C.F.R. § 1.132 dated Aug. 15, 2014 filed in Reexam. Control Nos. 90/011,869 and 90/011,869.
Declaration of Richard Chamberlin Under 37 C.F.R. § 1.132 dated Aug. 28, 2014.
Del Compo et al., "Creatinine, creatine and protein in cooked meat products", Food Chemistry, vol. 63, No. 2, pp. 187Y190, 1998.
Del Pilar Garcia-Santos et al., "Reactivity of Amino Acids in Nitrosation Reactions and Its Relation to the Alkylating Potential of Their Products," J. Am. Chem. Soc., 2002, 124(10): 2177-2182.
Dessaignes et al., The Chemist or Chemical & Physical Science, 1854, pp. 594-597.
Dhar et al., Complex Compounds of Acid, Base and Salt with Nitrogenous and Other Organic Substances, in National Academy of Sciences, India, Symposium on Nitrogen, Part 1, Section A, vol. 31, 1961, pp. 76-79.
Dhas, S.A. Martin Britto et al., Growth and Characterization of a New Organic NLO Material; Glycine Nitrate, ScienceDirect, Optics communications 278 (2007) 434-438.
Di Pasquale MG. Amino Acid and Proteins for the Athelete: The Anabolic Edge. CRC Press LLC, 1997, pp. 99-145.
Duncan et al., "Chemical generation of nitric oxide in the mouth from the enterosaliary circulation of dietary nitrate," Nature Medicine, 1 (6): 546-551, Jun. 1995.
Dymatize Nutrition, "Pre-Workout", http://www.dymatize.com/nitric-oxide, Mar. 31, 2014—Advertisement.
Dymatize Nutrition, "Xpand 2x 10 Serving—Dymatize Nutritional Supplements, Whey Protein, Bodybuilding", http://www.dymatize.com/store/p/289-Xpand-2x-10-Servings.html—Advertisement.
Dymatize® Xpand 2x®, Fruit Punch, Dymatize—GNC, www.gnc.com/product/index.jsp? productId=13180805, Jun. 17, 2013, p. 1-2.

(56) References Cited

OTHER PUBLICATIONS

EAS advertisement for "Phosphagen Elite" Joe Welder's Muscle & Fitness, Sep. 2005.
Eaton et al., "Urinary Beta-Alanine Excretion is a Marker of Abnormal as well as Normal Gut Fermentation", Journal of Nutritional & Environmental Medicine (Jun. 2004) 14(2), 121-127.
Edwards et al., "Amino Acids in Foods, Cystine, Tyrosine, and Essential Amino Acid Contents of Selected Foods", Agricultural and Food Chemistry, vol. 3, No. 11 , Nov. 1955.
Elkayam et al. "Prevention of nitrate tolerance with concomitant administration of hydralazine" Can J CArdiol,1996, vol. 12, suppl C, pp. 17C-21C. (Year: 1996).
Elmore et al., "Compilation of free amino acid data for various food raw materials, showing the relative contributions of asparagine, glutamine, aspartic acid and glutamic acid to the fee amino acid composition", Oct. 2002, JIFSAN Acrylamide in Food Workshop, Chicago. (Year 2002).
English translation of KR-20110015141-A, Feb. 15, 2011, pp. 1-23 (Year: 2011).
Eppendorfer et al., "Free and Total Amino Acid Composition for Edible Pears, Beans, Kale, Spinach, Cauliflower, and Potatoes as Influenced by Nitrogen Fertilisation and Phosphorus Deficiency," J.Sci. Food Agric. 71 449-458, 1996.
Eto et al. publication, Archives of Physiology and Biochemistry, 1995, 103(2):160-4.
Examine.com, "L-Carnitine", Sep. 12, 2014, https://examine.com/supplements/l-carnitine/. (Year:2014).
F. Murad, Cyclic Guanosine Monophosphate as a Mediator of Vasodilation, J. Clin. Invest., vol. 78, pp. 1-5 (Jul. 1986).
F. Ray, Meat Curing, ANSI-3994, OSU.
Fanous, S. "Is Sodium Nitrate Bad for You?", May 20, 2015, Healthline, https://www.healthline.com/health/food-nutrition/is-sodium-nitrate-bad-for-you#1, pp. 1-8. (Year: 2015).
Fayers et al."Nitrate tolerance and the links with endothelial dysfunction and oxidative stress," Br J Clin Pharmacol 56:620-628 (2003).
FDA Regulation 42 FR, 1977.
FDA Regulation 48 FR 1701, Indirect Food Additives; Paper and Paperboard Components, FDA, 1983.
Feelisch et al., Eur J. Pharmacol., 1987, 139(1):19-30.
Fetih et al."Excellent Absorption Enhancing Characteristics of No Donors for Improving the Intestinal Absorption of Poorly Absorbable Compound Compared with Conventional Absorption Enhancers," Drug Metab. Pharmacokinet. vol. 21(3):222-229 (2006).
Fetih et al."Nitric oxide donors can enhance the intestinal transport and absorption of insulin and [Asu1,7]-eel calcitonin in rats," Journal of Controlled Release 106:287-297 (2005).
Flaherty, 1989, Drugs, 137:523-550.
Fraser et al. publication, circulation, 1983, 67(2): 405-412.
G. M. McKnight, et al., Chemical synthesis of nitric oxide in the stomachfi-om dietary nitrate in humans, Gut, vol. 40, pp. 211-214 (1997).
G. M. McKnight, et al., Dietary nitrate in man: friend or foe?, British Journal of Nutrition, vol. 81, pp. 349-358 (1999).
G. R. J. Thatcher, Serial Review: Mechanisms and Novel Directions in the Biological Applications of Nitric Oxide Donors, Free Radical Biology & Medicine, vol. 37, No. 8, pp. 1122-1143 (2004).
G. Richardson, et al., The ingestion of inorganic nitrate increases gast,-;c S-nitrosothio/ levels and inhibits platelet unction in humans, Nitric Oxide, vol. 7, pp. 24-29 (2002).
G.S. Stokes, et al., Long-Term Effectiveness of Extended-Release Nitrate for the treatment of Systolic Hypertension, Hypertension vol. 45, pp. 380-384 (2005).
Gao et al., "Agmatine: A Novel Endogenous Vasodilator Substance," Life Sciences, 57(8): 83-86, 1995.
Gao et al., Life Science, 1995, 57: 83-86.
Giant Sport Metabolic Bioshock—Workout Supplement, on line, sale product, 2014.
Gibson et al. "Protective role of the epithelium of the small intestine and colon", inflamm. Bowel Dis., 1996, vol. 2, No. 4, pp. 279-302, abstract provided. (Year: 1996).
GNC Mega Men, "GNC Mega Men 90 Caplets", http://www.gnc.com/GNC-Mega-Men-reg/product.jsp?productId=4033432, Apr. 22, 2014.
Godzisz, "Classification and nature of hydrogen bonds to betaine. X-ray, 13C CP MAS and IR description of low barrier hydrogen bonds," Journal of Molecular Structure, 606:123-137,2002.
Grasemann et al., "Oral L-arginine supplementation in cystic fibrosis patients: a placebo-controlled study," Eur Respir J 25:62-68 (2005).
Green et al. publication, Sports Med., 1996, 21(2): 119-146.
Gwartney, D. L, "On the Horizon: Agmatine," Oct./Nov. 1998, Pump 101:96-97.
Harm J. Knot. "Nitrate Tolerance in Hypertension New Insight Into a Century-Old Problem," Circulation Research vol. 93:799-801 (2003).
Harrison, D.G. et al., "The Nitrovasodilators, new Ideas About Old Drugs," Circulation, vol. 87, No. 5, May 1993, pp. 1461-1467).
Hatanaka et al."Stereoselective Pharmacokinetics and Pharmacodynamics of Organic Nitrates in Rats," J Pharmacol Exp Ther. vol. 298(1):346-53 (2001).
Haussuhl, "Elastic and thermoelastic properties of twelve adducts of betaine," Z Kristallogr, 188:311-320,1989.
Hayashi et al.PNAS 102(38):13681-13686 (2005).
Henriksson et al., Acta Physiol, Sep. 1, 2007, 191:1.
Herbwisdom.com, 2006.
Hoffman et al., "Effect of Creatine and β-Alanine Supplementation on Performance and Endocrine Responses in Strength/Power Athletes", International Journal of Sport Nutrition and Exercise Metabolism, 2006, 16, 430-446, © 2006 Human Kinetics, Inc.—20.
Honikel's publication, Meat Science, 2008,78: 68-76.
Hord et al., "Food sources of nitrates and nitrites: the physiologic context for potential health benefits1-3", Perspective, Am J Clin Nutr 2009;90:1-10, American Society for Nutrition.
http://www.beyondsupplements.com.au/index.php?route=product/, no date given.
http://www.bodybuilding.com/store/fuel-one/6th-gear.html, no date given.
http://www.curezone.org, no date given.
http://www.dymatize.com/store/workoutsupport/M-P-ACT-Energy, no date given.
http://www.ergo-log.com/plaatjes/xpand2x.gif, no date given.
https://nuts.com/cookingbaking/powders/beet.html, 2016.
https://www.thesynergycompany.com/organic-carrot-juice-powder, no date given.
Hui or Shi et al., Handbook of Food Science, Technology, and Engineering, 2006, vol. 4, Chapter 170, p. 170-1-170-9.
Hunter et al., "The Inhibition of Arginase By Amino Acids", Department of Pathological Chemistry, University of Toronto, Canada, Jul. 24, 1944.
Huxtable et al. Physiological Reviews, 72(1):101-142, 1992.
IForce Nutrition product "Potassium Nitrate", 2006.
Ignarro ("After 130 years, the molecular mechanism of action of nitroglycerin is revealed,"[online], Jun. 11, 2002 [retrieved on May 8, 2016] Retrieved from the Internet: <http://www.pnas.org/cgi/content/full/99/12/7816?ck=nck>).
Ignarro et al. publication, The Journal of Pharmacology and Experimental Therapeutics, 1988, 244(1): 181-189.
Ignarro et al., "Pharmacology of Endothelium-derived Nitric Oxide and Nitrovasodilators", The Western Journal of Medicine, Jan. 1991, 154.
Ilczyszyn et al. CAS: 145:836302006.
Ingested Nitrate and Nitrite, and Cyanobacterial Peptide Toxins, World Health Organization International Agency for Research on Cancer (2010).
Ionic Liquids ( URL: https://www.organic-chemistry.org/topics/ionic-liquids.shtm ), printed Apr. 2019 (Year: 2019).
Ishii et al., "High glucose augments arginase activity and nitric oxide production in the renal cortex," Metabolism 53(7):868-874 (2004).

(56) References Cited

OTHER PUBLICATIONS

J. Abrams, MD, Beneficial Actions of Nitrates in Cardiovascular Disease, The American Journal of Cardiology, vol. 77, p. 31C-37C (May 30, 1996).
Jablecka et al.Med Sci Monit 10(I):CR29-32 (2004).
Jamalian et al., "Nutritional Value of Middle Eastern Foodstuffs", Jamalian & Pellett : Nutritional Value of Middle Eastern Foodstuffs. IV, Dec. 1967.
Joy et al., "A multi-ingredient, preworkout supplement is apparently safe in healthy males and females," Food & Research, 59:27470, 2015.
K. Cosby, et al., Nitrite reduction to nitric oxide by deoxyhemoglobin vasodilates the human circulation, Nature Medicine, vol. 9, No. 12, pp. 1498-1505(Dec. 2003).
K. Tsuchiya, et al., Malfunction of Vascular Control in Lifestyle-Related Diseases: Formation of Systemic Hemoglobin-Nitric Oxide Complex (HbNO) From Dietary Nitrite, J. Pharmacol Sci, vol. 96, pp. 395-400 (2004).
Kemmerer et al. publication, J. Nutr., 1949, 38(4): 527-33.
Kendrick et al., "The effect of 4 weeks B-alanine supplementation and isokinetic training on carnosine concentrations in type I and II human skeletal muscle fibres", Eur J Appl Physiol (2009) 106:131-138, Feb. 12, 2009.
Kenechuwu et al. J. Microencapsul, 2017, 34(6):592-609.
Kernohan et al., "An oral yohimbine/L-arginine combination (NMI 861) for the treatment of male erectile dysfunction: a pharmacokinetic, pharmacodynamic and interaction study with intravenous nitroglycerine in healthy male subjects", British Journal of Clinical Pharmacology, © 2004 Blackwell Publishing Ltd.
Kou et al. applicaiton No. 200410009958.3, 2005.
Kramer et al., U. S. Patent Application Publication No. 2009/076110 A1 published Mar. 19, 2009.
L. Appel, et al., A Clinical Tr;al of the Effects of Dietal J1 Patterns on Blood Pressure, N. Engl. J. Med., 336:16, pp. 1117-1124 (Apr. 17, 1997).
L. Brunton, An Address on Blood Pressure In Man: Its estimation and indications for treatment, The British Medical Journal, pp. 64-67 (Jul. 10, 1909).
L. Brunton, et al., An Address on Longevity and the Means of Attaining It, The Lancet, vol. 168, Issue 4342, pp. 1330-1335 (Nov. 17, 1906).
L. Noah et al., Starting from Scratch?: Reinventing the Food Additive Approval process, Boston Univ. L. Rev. vol. 78:329, pp. 329-443.
L. Stryer, Biochemistry, Third Edition, W. H. Freeman and Company, pp. 15-24, 261-268, 499-502, and 933-936, New York, 1988.
Large Wendy, "Circuit training combines aerobic and anaerobic workouts into one," News Journal (Mansfield Ohio), Sep. 5, 2004.
Larsen et al. publication, New England Journal of Medicine, 2006, 2792-2793.
Larsen, Effects of dietary nitrates on oxygen cost during Exercise, B. Acta Physiol 191(1 ):59-66 (2007).
Lewis et al. publication, Pharmacol. Biochem Behav, 2007, 88(1): 114-21.
Ilczyszyn et al. 13C chemical shift tensors of hydrogen bonded amino acids: Relations between experimental and calculated results. Chemical Physics 323 (2006) 231-242.
Luigi et al., Med. Sc.i Sports Exerc., 1999, 31(12): 1748-54.
Lundberg et al., "Cardioprotective effects of vegetables: Is nitrate the answer?", Science Direct, Jan. 2006.
Lundberg et al., "The nitrate-nitrite-nitric oxide pathway in physiology and therapeutics", 2008 Nature Publishing Group, Feb. 2008, vol. 7.
Lundberg et al., Arterioscler. Thromb. Vasc. Biol., 25:915-922 (2005).
Lundberg et al., Inorganic nitrate is a possible source of systemic generation of nitric oxide, Free Radical Biology Medicine, vol. 37, No. 3. pp. 395-400, 2004.
Luscher, "Endogenous and exogenous nitrates and their role in myocardial ischaemia," Br. J. Clin. Pharmacol. 34:29S-35S (1992).

Magg, G.W., Hecker, R.J. and Whitaker, P.A., "Nitrogenous Compounds in Sugarbeet Juices", Journal of the American Society of Sugar Beet Technologists, 1972; vol. 17, No. 2pp. 154-164.
Marconi, Int. J. Sports Med, 11 (1990):1-14.
Material Safety Data Sheet—L-leucine MSDS.
Material Safety Data Sheet—Taurine.
Material Safety Data Sheet—Agmatine sulfate salt.
Material Safety Data Sheet—B-Alanine MSDS.
Material Safety Data Sheet—L-Arginine.
Material Safety Data Sheet—L-Glutamine MSDS.
Material Safety Data Sheet—L-Norvaline.
Maynard et al., "High Levels of Dietary Carnosine Are Associated with Increased Concentrations of Carnosine and Histidine in Rat Soleus Muscle," J. Nut. 131:287-290 (2001).
Merriam-Webster definition of supplement https://www.merriam-webster.com/dictionary/supplementlaccessed Jun. 20, 2019] (Year: 2019).
Miller, Elements of Chemistry—Theoretical and Practical, Longsmans, Green, Reader and Dyer, 1969, pp. 757-770.
Ming et al.Circulation 110:3708-3714 (2004).
Mostad et al."Crystal and molecular structure of DL-methionine nitrate," CAS 104:1975, 43 (1986).
Mostad, A., Zeitschrift fur Kristallographie, 172: 175-182, 1985.
MrSupplement.com product dietary supplement Creatine Nitrate, 2006.
Muramoto, J., "Comparison of Nitrate Content in Leafy Vegetables from Organic and Conventional Farms in California" Center for Agroecology and Sustainable Food Systems University of California, Santa Cruz, 1999.
Nature's Best advertisement for "Perfect L-Glutamine" Joe Weider's Muscle & Fitness, Sep. 2005.
Niu et al."Vasorelaxant effect of taurine is diminished by tetraethylammonium in rat isolated arteries," European Journal of Pharmacology 580:169-174 (2008).
NutrabioBCAA2500, 2006.
Oka et al.Vasc Med 10:265-274 (2005).
Optimum Nutrition advertisement for "Adenergy Stack" Joe Weider's Muscle & Fitness, Sep. 2005.
Pariser et al. Cutis, 1994, 54(1): 43-44.
Parker et al., The Effect of Supplemental L-Arginine on Tolerance Development During Continuous Transdermal Nitroglycerin Therapy, J. of Am. Coll. of Cardiology, 39(7): 1199-1203, 2002.
PEScience High Volume, 2007.
Petersson et al., "Dietary nitrate increases gastric mucosal blood flow and mucosal defense," Am. J. Physiol. Gastrointest. Liver, 292: G718-G724, 2007.
Petrosyan et al., J. Molecular Structure, 794: 160-167, 2006.
Piccolo et al. CAS: 138: 1375892003.
Pickering et al., Why Don't We Use Nitrates to Treat Older Hypertensive Patients?, Journal of Clinical Hypertension, vol. 7, No. 11, pp. 685-690 (Nov. 2005).
Pischel et al. CAS: 134:71896, 2001.
Pradhan et al., Journal of Chemical and Engineering Data, 2000, 45(1):140-143.
ProArgi 9 Supplement Website: ProArgi-9 Plus FAQ, "ProArgi 9 Plus Site", http://proargi9site.blogspot.com/p/proargi-9-plus-faq.html, Apr. 22, 2014.
Professor of Udinsev. Nitrates and physical performance. Siberian fiber. Sep. 8, 2018. [on-line] [ retrieved on Jun. 29, 2020] (Retrieved from the Internet: https://tfzp.ru/zdorovyj-obraz-zhizni/v/nitraty/nitraty-i-fizicheskaya-rabotosposobnostO, p. 2, paragraph 2—p. 3, paragraph 1, p. 4, paragraph 1.
PS Nutrition Creatine Nitrate, on line, sale producr, 2014.
QuadraLean by RSP Nutrition, Bodybuilding.com, 2006.
R.C. Harris et al., "The Influence of Beta-Alanine Supplementation and Training on the Muscle Carnosine Content in Human v. lateralis, and the Effect of This on Exercise Performance," Amino Acids 29:12-13 (2005).
Rajkumar and Ramakrishnan, "Infrared and Roman Spectra of L-Valine Nitrate and L-Leucine Nitrate", Journal of Raman Spectroscopy, 2000. p. 1107-1112, vol. 31. John Wiley & SonsLtd.

(56) References Cited

OTHER PUBLICATIONS

Rajkumar et al., "Infrared and Raman spectra of DL-aspartic acid nitrate monohydrate," Spectrochimica Acta Part A, 54:1527-1532, 1998.
Ramaswamy et al."Vibrational spectroscopic studies of L-argininium dinitrate," J. Raman Spectrosc. 34:50-56 (2003).
Rao et al."Structure and Conformational Aspects of the Nitrates of Amino Acids and Peptides. I. Crystal Structure of Glycylglycine Nitrate," Acta Cryst. B29:2379-2388 (1973).
Riens et al., "Amino Acid and Sucrose Content Determined in the Cytosolic, Chloroplastic, and Vacuolar Compartments and in the Phloem Sap of Spinach Leavesl", Plant Physiol. (1991) 97, 227-233, Apr. 6, 1991.
Rimando et al., "Determination of Citrulline in Watermelon Rind", Journal of Chromatography A, 1078 (2005) 196-200, May 2, 2005.
Rombauer, Irma S., "Joy of Cooking", 75th Anniversary, Scribner, New York, 2006, p. 163 (2006).
Romero et al., "Therapeutic Use of Citrulline in Cardiovascular Disease," Cardiovascular Drug Reviews 24(3-4):275-290 (2006).
Rosen et al. "Nutrient Management for Commercial Fruit & Vegetable Crops in Minnesota" University of Minnesota extension Service, 2005 pp. 35-36 <https://conservancy.umn.edu/bitstream/handle/11299/51272/5886.pdf?sequence=1 >.
RSPReGenBCAA, 2006.
Ruel et al., "Modulation in Angiogenic Therapy randomized controlled trial," J Thorac Cardiovasc Surg 135:762-770 (2008).
Rytlewski et al., Effects of prolonged oral supplementation with L-arginine on blood pressure and nitric oxide synthesis in preeclampsia, Eur J Clin Lnvest 35(1):32-37 (2005).
Rytlewski et al.European Journal of Obstetrics & Gynecology and Reproductive Biology 138:23-28 (2008).
S. Moncada, et al., The L-Arginine:Nit ic Oxide Pathway, Journal of Cardiovascular Pharmacology, 17(Suppl. 3):S 1-S9 1991).
S. Ramaswamy, Acta Cryst., E58, 646-648 (2002).
Sader et al., "Endothelial Function, Vascular Reactivity and Gender Differences in the Cardiovascular System", Cardiovascular Research 53 (2002) 597-604, Aug. 21, 2001.
San Corporation dietary supplement containing creatine nitrate, 2006.
Santamaria et al. "A survey of nitrate and oxalate content in fresh vegetables" Journal of the Science of Food and Agriculture, 1999, vol. 79, 1882-1888. (Year: 1999).
Sastre et al."Metabolism of agmatine in macrophages: modulation by lipopolysaccharide and inhibitory cytokines," Biochem. J. 330:1405-1409 (1998).
Schaefer et al., Intl. J. of Sports Medicine, 2002, 23(6):403-407.
Schulbach et al., "Guide to nitrogen quick-tests for vegetables wit the 'cardy' nitrate meter" FREP Contract #95/0582.
Schulz et al., "Functional and Biochemical Analysis of Endothelial (Dys)function and NO/cGMP Signaling in Human Blood Vessels with and without Nitroglycerin Pretreatment," Circulation 105:1170-1175 (2002).
Schwedhelm et al., "Pharmacokinetic and pharmacodynamics properties of oral L-citrulline and L-arginine: impact on nitric oxide metabolism," Br J Clin Pharmacol 65(1):51-59 (2007).
Sen et al. Journal of Association of Official Analytical Chemists, 61(6): 1389-1394, 1978.
Shen et al. publication, Acta Physiol. Scand, 2000, 168(4): 675-86.
Shen, W., Nitric oxide production and No. synthase gene expression contribute to vascular regulation during exercise, Med. Sri Spnrts Fxerc., vol. 27,No. 8, pp. 1125 1134(Aug. 1995).
Shiraki et al., "The hypotensive mechanisms of the new anti-anginal drugN-(2-Hydroxyethyl) Nicotinamide Nitrate (SG-75) in beagle dogs," Japan. J. Pharmacol, vol. 31:921-929 (1981).
Slart et al., "Nitrate Administration Increases Blood Flow in Dysfunctional but Viable Myocardium, Leading to Improved Assessment of Myocardial Viability: A Pet Study," J Nucl Med 47:1307-1311 (2006).
Smith et al."Nitric oxide precursors and congenital heart surgery: A randomized controlled trial of oral citrulline," J Thorac Cardioasc Surg 132:58-65 (2006).
Sridhar et al., "L-Aspartic Acid Nitrate-L-Aspartic Acid," Acta Cryst. E58:o1372-o1374 (2002).
Srinivasan et al., "L-phenylalanine-nitric acid (2/1)," Acta Crystallographica E57:o916-o918, 2000.
Stephany et al. "The Intake of Nitrate, Nitrite and Volitile N-Nitrosamins and the Occurrence of Volatile N-nitrosamines in human urine and Veal Calves" IARC Scientific Publications, Jan. 1978, vol. 19, pp. 443-460. (Year: 1978).
Stephenson, T., "How children's responses to drugs differe from adults," Br. J. Clin. Pharmacol., 59(6):670-673, 2005.
Stetson, C., "Characteristics of Adults vs. Children." [retrieved on May 4, 2016], Retrieved from the Internet <URL: http://www.ehow.com/info 8501147 characteristics-adults-vs-children.html>.
Stout et al., "Effects of B-Alanine Supplementation on the onset of Neuromuscular Fatigue and Ventilatory Threshold in Women", Amino Acids (2006), Springer-Verlag 2006.
Stryer, Lubert, Biochemistry, Third Edition, W.H. Freeman and Company, New York: 1988, pp. 16-23, 233-236, 500-502 and 934-936.
Sugino et al., "L-ornithine supplementation attenuates physical fatigue in healthy volunteers by modulating lipid and amino acid metabolism," Nutrition Research, 2008, 28:738-743.
Summary of Studies of B-Alanine and sports performance, "Studies of B-Alanine Supplementation on Exercise Capacity or Performance", Nov. 2011.
Swensen et al. publication, Intl. J. of Sports medicine, 1994,15(7):430-4.
Takahashi et al."Characterization of the influence of nitric oxide donors on intestinal absorption of macromolecules," International Journal of Pharmaceutics 286:89-97 (2004).
Tan et al., "Taurine protects against low-density lipoprotein-induced endothelial dysfunction by the DDAH/ADMA pathway," Vascular Pharmacology 46:338-345 (2007).
Tannebaum et al., "Inhibition of nitrosamine formation by ascorbic acid," Am. J. Clin. Nutr. 53: 2475-2505, 1991.
Tao, Guo-Hong et al., new Generation Ionic Liquids: Cations Derived From Amino Acids, The Royal Society of Chemistry, ChemComm, Jun. 9, 2005, 3562-3564.
Taurine from Nutrabio, 2006.
Teragawa et al. (Heart, 86:212-216, 2001) Magnesium causes nitric oxide independent coronary artery vasodilation in humans.
Terzyan et al., "L-Arginine Nitrates," Journal of Molecular Structure 687:111-117 (2004).
Thandani, U. "Challenges with Nitrate Therpy and Nitrate Tolerance: Prevalence , Prevention, and Clinical Relevance" Am J Cardiovasc Drugs, 2014, vol. 14, pp. 287-301. (Year: 2014).
The product APS Creatine Nitrate , for sale, 2014.
The product Isoleucine nitrate power with a Brand name Hobid, for sale, 2014.
The product L-glutamine nitrate power with a Brand name Hobid, for sale, 2014.
The product L-Leucine nitrate power by Body Ripped, for sale, 2014.
The product valine nitrate power with a Brand name Hobid, for sale, 2014.
U.S. Food & Drug Administration document with respect to 21 CFR §184.1878 for thiamine mononitrate (Year: 2018).
USDA and HHS Agencies Work Together to Examine the Jurisdiction of Certain Food Categories, USDA & FDA, 2005.
USDA Regulation 64 FR 72168, Food Ingredients and Sources of radiation Listed or Approved for Use in the Production of Meat and Poultry, 1999.
Vandenberghe et al. publication, J. Appl physiol, 1997, 83:2055-2063.
VS Kouzenkov, AL Krushinsky , "Sodium potassium effect on development of nerological deficiency in experimental model of brain ishemia", Moscow University Bulletin Ser. 16. Biology, (20140000), vol. 4, pp. 9-14, XP055831436.
Vytech advertisement for "Nitrobol Extreme" Joe Welder's Muscle & Fitness, Sep. 2005.

(56) References Cited

OTHER PUBLICATIONS

Walker et al., Food additive and Contaminants, 1990, 7(6):717-768.
Watt et al., "The Chemist, A Monthly Journal of Chemical & Physical Science", vol. 1, London; Samuel Highley, 32 Fleet Street, 1854.
Watts, "A Dictionary of Chemistry and the Allied Branches of Other Sciences", Library of the University of California, Aug. 1808.
Weitzberg et al., "Dietary Nitrate—A Slow Train Coming", J Physiol 589.22 (2011) pp. 5333-5533, 2011 The Authors. Journal compilation, 2011 The Physiological Society.
Wheatley et al., "Arginine deprivation and tumor cell death arginase and its inhibition," Molecular and Cellular Biochemistry, 244: 177-185, 2003.
White, Handlerand Smith, Principles of Biochemistry, Fifth Edition, McGrawy-Hill, New York:1973, pp. 89-95.
Winter et al., "N-Nitrosamine Generation From Ingested Nitrate Via Nitric Oxide in Subjects With and Without Gastroesophageal Reflux," Gastroenterology, 2007, 133:164-174.
Ximenes, M. I. N., et al., "Polarographic determination of nitrate in vegetables" Talanta 51 (2000) 49-56.
Xu et al., "Composite medical preparation for promoting hair growth," CAS: 143:103285 (2005).
Zhang et al. publication, Amino acids, 2004, 26:203-207.
Zhu et al., "Expression of Human Arginine Decarboxylase, the Biosynthetic Enzyme for Agmatine", NIH Public Access, Biochim Biophys Acta. Jan. 22, 2004; 1670(2): 156-164.
Ziegenfuss et al., "Effect of a Supplement Containing Primarily Beta Alanine, Arginine, Creatine Malate, and Glycerol Monostearate on Exercise-Induced Changes in Lean Mass of the Arms", Journal of the International Society of Sports Nutrition 2008, 5(Suppl 1):P16 doi: 10.1186/1550-2783-5-S1-P16.

* cited by examiner

N-ACETYL BETA ALANINE METHODS OF USE

CROSS REFERENCE TO RELATED APPLICATION

This application is a continuation application of the earlier U.S. Utility patent application to Ronald Kramer, et. al. entitled "N-Acetyl Beta Alanine Methods of Use," application Ser. No. 13/446,416, filed Apr. 13, 2012, which application claims the benefit of the filing date of U.S. Provisional Patent Application 61/475,179 entitled "N-Acetyl Beta Alanine Methods of Use", filed on Apr. 13, 2011, the disclosures of all which being hereby incorporated entirely herein by reference.

BACKGROUND

1. Technical Field

Aspects of this document relate generally to n-acetyl beta alanine and methods of use.

2. Background

β-Alanine (or beta-alanine) is a naturally occurring beta amino acid, which are amino acids in which the amino group is at the β-position from the carboxylate group. Its structure is as follows:

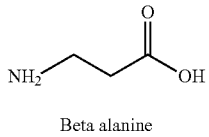

Beta alanine

β-Alanine is not used in the biosynthesis of any major proteins or enzymes. It is formed in vivo by the degradation of dihydrouracil and carnosine. It is a component of the naturally occurring peptides carnosine and anserine and also of pantothenic acid (vitamin B5) which itself is a component of coenzyme A. Under normal conditions, β-alanine is metabolized into acetic acid.

β-Alanine is the rate-limiting precursor of carnosine, which is to say carnosine levels are limited by the amount of available β-Alanine. Carnosine removes excess acid from the muscle cell, thus reducing fatigue, etc. Therefore, the beneficial effects described for beta-alanine also apply to carnosine. Supplementation with β-alanine has been shown to increase the concentration of carnosine in muscles, decrease fatigue in athletes and increase total muscular work done.

See for example the following publications. In "Muscle carnosine metabolism and beta-alanine supplementation in relation to exercise and training", Derave et al., Sports Med. 2010 Mar. 1; 40(3):247-63, the researchers have made an extensive review of beta-alanine's physiological role, it's effects and it's ability to enhance sports performance. In "The effects of 10 weeks of resistance training combined with beta-alanine supplementation on whole body strength, force production, muscular endurance and body composition", Kendrick et al., Amino Acids. 2008 May; 34(4):547-54 it was exhibited that beta alanine supplementation can enhance muscle carnosine levels. In "Beta-alanine supplementation reduces acidosis but not oxygen uptake response during high-intensity cycling exercise", Baguet et al., Eur J Appl Physiol. 2010 February; 108(3):495-503, it was described that beta alanine supplementation at 4.8 grams per day can attenuate acidosis due to exercise, resulting in increased performance in some models.

β-Alanine, therefore, finds great use in sports supplements to reduce muscle fatigue, muscle damage, promote endurance, promote recovery, increase strength and improve athletic performance and body composition. Apart from these uses beta-alanine may be used for the treatment of muscle wasting diseases, in anti-aging formulas, in overall health formulas and any other use where increased muscular performance is wanted. The effective doses used in studies range from 2.4 grams per day (see for example, "The effect of beta-alanine supplementation on neuromuscular fatigue in elderly (55-92 Years): a double-blind randomized study", Stout et al., Journal of the International Society of Sports Nutrition 2008, 5:21, where supplementation of 800 mg×3 per day resulted in 28% increase in physical working capacity fatigue threshold) to as much as 6 grams per day, although it is not uncommon to see supplements with lower (as little as 500 mg) or larger doses.

Despite the foregoing, beta alanine's use still suffers from drawbacks. The biggest drawback of beta alanine use is paresthesia, a "tingling" sensation users experience that comes from reaction of beta alanine with nerves of the skin. Symptoms of paresthesia start at doses as low as 800 mg (see, for example, "Role of beta-alanine supplementation on muscle carnosine and exercise performance", Artioli et al., Med Sci Sports Exerc. 2010 June; 42(6):1162-73, where it is mentioned that "Symptoms of paresthesia may be observed if a single dose higher than 800 mg is ingested") and can worsen with higher doses. This is so uncomfortable to some users that they opt to use beta alanine in many small servings during the day or just not all.

Another drawback of beta alanine is that while it is water soluble, it is very poorly soluble in organic solvents. Beta alanine is described to have a water solubility of 55-89 grams/100 ml. This makes it extremely hydrophilic and lipophobic, which may hinder it's capacity to bypass certain cell membranes like the blood-brain barrier (see, for example, "Determination of lipophilicity and its use as a predictor of blood-brain barrier penetration of molecular imaging agents", Waterhouse, Mol Imaging Biol. 2003 November-December; 5(6):376-89, where it is described how increasing lipophilicity increases blood-brain barrier permeation) or the muscle cell wall by passive diffusion. Although beta alanine is transported by an active transport system (see, for example, "Sodium and chloride ion-dependent transport of beta-alanine across the blood-brain barrier", Komura et al., J. Neurochem. 1996 July; 67(1):330-5, where Komura et. al. describe how beta-alanine can be transported via the Blood Brain Barrier by a sodium/chloride dependent channel) it would be desirable to increase absorption rate by adding passive diffusion to the absorption mechanisms (increasing lipophilicity can increase permeation and absorption through biological membranes).

SUMMARY

In one aspect, a method for increasing athletic performance in a human or animal is disclosed. The method includes administering to the human or animal a pharmaceutically effective amount of N-Acetyl Beta Alanine.

In another aspect, a method for preventing paresthesia in a human or animal is disclosed. The method includes administering to the human or animal a pharmaceutically effective amount of N-Acetyl Beta Alanine.

In still another aspect, a method for increasing beta alanine absorption and cell membrane permeability through both passive diffusion and active transport in a human or animal is disclosed. The method includes administering to the human or animal a pharmaceutically effective amount of N-Acetyl Beta Alanine.

In yet another aspect, a method for increasing the half-life of beta alanine present in a blood stream in a human or animal is disclosed. The method includes administering to the human or animal a pharmaceutically effective amount of N-Acetyl Beta Alanine.

Implementations may comprise one or more of the following.

The methods may include administering a pharmaceutically effective amount of an N-Acetyl Beta Alanine composition including N-Acetyl Beta Alanine and a pharmaceutically acceptable additive. The additive may be a carrier, excipient, binder, colorant, flavoring agent, preservative, buffer, dilutant, or any combination thereof.

N-Acetyl Beta Alanine or N-Acetyl Beta Alanine composition may be in the form of a capsule, tablet, pill, liquid, liquid suspension, vapor, gas, powder, granulate or pulverulence.

Advantages of administering an N-acetyl beta alanine alone or as part of a Composition are:

Elimination of the paresthesia side-effect that is typically present in administration of beta alanine without the inconvenience and added cost of devising multiple small dose regimes or time-released forms that have been suggested in the past.

Higher lipophylicity without eliminating water-solubility, therefore, asserting greater absorption and cell membrane permeability through both passive diffusion and active transport.

Greater half life of beta alanine.

Totally improved effectiveness and ease of use compared to beta alanine.

The foregoing and other aspects, features, and advantages will be apparent to those artisans of ordinary skill in the art from the DESCRIPTION, and from the CLAIMS.

DESCRIPTION

Overview, Terminology and Definitions

In describing implementations of an N-acetyl beta alanine compounds or compositions and methods of use, the following terminology will be used in accordance with the definitions and explanations set out below. Notwithstanding, other terminology, definitions, and explanations may be found throughout this document, as well.

As used herein, "Composition" is a term used in its broadest sense and may refer to a mixture of constituent substances or ingredients. "Mixture" is a term used in its broadest sense and may refer to two or more constituent substances or ingredients (chemical species present in a system) which have been combined (not necessarily in fixed proportions and not necessarily with chemical bonding and not necessarily so that each substance retains its own chemical identity). Mixtures can be the product of a blending or mixing of chemical substances like elements and compounds, without chemical bonding or other chemical change, so that each ingredient substance retains its own chemical properties and makeup. Mixtures can be either homogeneous or heterogeneous. A homogeneous mixture is a type of mixture in which the composition is uniform. A heterogeneous mixture is a type of mixture in which the composition can easily be identified, as there are two or more phases present. A homogeneous mixture in which there is both a solute and solvent present is also a solution.

A "Compound" is a term used in its broadest sense and may refer to a chemical substance comprising two or more different chemically bonded chemical constituent elements or ingredients, with a fixed ratio or proportion by weight. The atoms within a compound can be held together by a variety of interactions, ranging from covalent bonds to electrostatic forces in ionic bonds. The physical and chemical properties of compounds are different from those of their constituent elements. This is one of the main criteria for distinguishing a compound from a mixture of elements or other substances because a mixture's properties are generally closely related to and dependent on the properties of its constituents. However, some mixtures are so intimately combined that they have some properties similar to compounds. Another criterion for distinguishing a compound from a mixture is that the constituents of a mixture can usually be separated by simple, mechanical means such as filtering, evaporation, or use of a magnetic force, but the components of a compound can only be separated by a chemical reaction. Conversely, mixtures can be created by mechanical means alone, but a compound can only be created (either from elements or from other compounds, or a combination of the two) by a chemical reaction.

Thus, for purposes of this disclosure, "Composition" may refer to a mixture of at least N-acetyl beta alanine in combination with some other component or constituent.

As used herein, "N-acetyl beta alanine" is a term used in its broadest sense and may refer to 3-acetamidopropanoic acid, N-Acetyl-beta-alanine, 3-acetamidopropanoic acid, and 3-(acetylamino)propanoic acid. It has a molecular formula of $C_5H_9NO_3$ and a molecular weight of 131.129860 [g/mol]. It appears as a white fine powder and is odorless and soluble in water and organic solvents.

It also may refer to its many different chemical forms including its physiologically active salts or esters or chelates, its combinations with its various salts, its tautomeric, polymeric and/or isomeric forms, its analog forms, and/or its derivative forms.

It also may refer to other amides of beta alanine. An example would be N-butyl beta-alanine or N-isopropyl beta alanine. Furthermore after the acetylation has taken place, further modifications of the molecule could take place, like etherification of the carboxylic group wielding for example n-acetyl beta-alanine ethyl-ester or n-acetyl beta-alanine methyl ester. Another modification would be the use of different salts of the acetylated beta alanine, like n-acetyl beta alanine nitrate, Sodium n-acetyl beta alanine, etc.

For the exemplary purposes of this disclosure, the structure of N-acetyl beta alanine and some of the other chemical forms mentioned above are shown below:

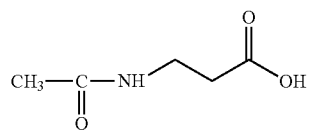

N-acetyl beta alanine

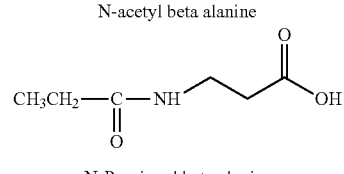

N-Propionyl beta alanine

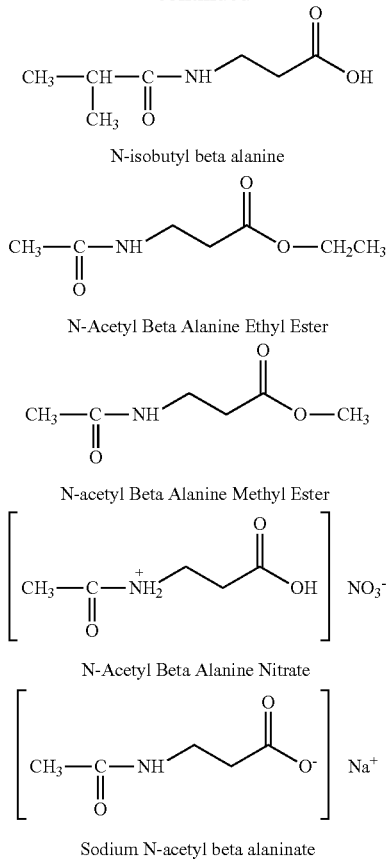

N-isobutyl beta alanine

N-Acetyl Beta Alanine Ethyl Ester

N-acetyl Beta Alanine Methyl Ester

N-Acetyl Beta Alanine Nitrate

Sodium N-acetyl beta alaninate

As used herein, "pharmaceutically acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

As used in this document, "pharmaceutically effective" is a phrase used in its broadest sense, including, by non-limiting example, effective in a clinical trial, for a specific patient, or only placebo-effective.

As used in this document, "Pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

Components/Compounds/Compositions

N-acetyl beta alanine is an existing naturally occurring beta-alanine analog that has not been administered in humans for enhancing athletic performance or any other purpose for which beta-alanine is used.

In the body, N-acetyl beta alanine is de-acetylated by the enzyme N-acetyl beta alanine deacetylase. N-acetyl-beta-alanine deacetylase (ENZYME entry: EC 3.5.1.21) is an enzyme that catalyzes the chemical reaction: N-acetyl-beta-alanine+$H_2O$⇌acetate+beta-alanine. Thus, the two substrates of this enzyme are N-acetyl-beta-alanine and $H_2O$, whereas its two products are acetate and beta-alanine. This enzyme belongs to the family of hydrolases, those acting on carbon-nitrogen bonds other than peptide bonds, specifically in linear amides. The systematic name of this enzyme class is N-acetyl-beta-alanine amidohydrolase. This enzyme participates in beta-alanine metabolism.

Even though N-acetyl-beta-alanine and beta alanine have some similar structure, there is evidence showing there is no reasonable expectation of similar properties. As evidence that N-acetyl beta alanine is not an equally functioning beta alanine analog (but rather a higher functioning one), when compared to other beta alanine forms, N-acetyl beta alanine offers very different properties, such as improved cell permeability, longer half-life and more importantly no paresthesia observed even at large doses of 5+ grams. N-acetyl-beta-alanine was found by applicants to possess a solubility in water of 22 g/100 mg-enough for all practical purposes—but yet less hydrophilic than beta alanine.

The N-acetyl form of beta alanine cannot react with nerve ends to produce paresthesia since amides are neurologically inactive. Therefore, by slowly converting to beta-alanine through deacetylation, paresthesia is prevented due to low but constant blood-serum beta alanine concentrations. This also increases the half-life of beta-alanine present in the blood stream and cell membrane permeability.

Thus, advantages of administering an N-acetyl beta alanine alone or as part of a Composition are:

Elimination of the paresthesia side-effect that is typically present in administration of beta alanine without the inconvenience and added cost of devising multiple small dose regimes or time-released forms that have been suggested in the past.

Higher lipophylicity without eliminating water-solubility, therefore, asserting greater absorption and cell membrane permeability through both passive diffusion and active transport.

Greater half life of beta alanine.

Totally improved effectiveness and ease of use compared to beta alanine.

For the exemplary purposes of this disclosure, N-acetyl beta alanine could be used either as a nutritional supplement or a pharmaceutical composition.

An exemplary composition of N-acetyl beta alanine to enhance performance in athletes (in powder form to be mixed with water and drunk once per day, preferably before training on training days) is: N-acetyl-beta-alanine 6 grams; Creatine Nitrate 5 grams; and Vitamin C 300 mg.

An exemplary composition containing N-acetyl beta alanine to prevent neuronal damage in diabetics is: Ascorbic Acid 200 mg; Alpha Lipoic Acid 100 mg; N-acetyl-Beta-Alanine 3 grams; and Vitamin E (as gamma tocopherol) 10.000 IU.

An exemplary composition containing N-acetyl beta alanine to be used as an antiaging supplement is: Resveratrol 300 mg; Piperine 10 mg; N-acetyl-beta alanine 2 grams; and Ecdysterone 200 mg.

Manufacture

Implementations of N-acetyl beta alanine Compounds or Compositions may be synthesized or created in a wide variety of manners, and may be made from a wide variety of materials. Those of ordinary skill in the art will readily be able to select appropriate materials and methods to manufacture and use the compounds and compositions disclosed herein.

Accordingly, although there are a variety of method implementations for producing pharmaceutical compositions, for the exemplary purposes of this disclosure, a method implementation for producing an N-acetyl beta alanine may include the reaction of isomolar quantities of beta-alanine and Acetyl chloride in aqueous solution or any other polar, easily evaporated solvent such as methanol, alcohol, pyridine, and the like. Catalysts such as triethylamine, pyridine or DMAP can be used to speed up the reaction while as bases they can be used to neutralize the produced hydrochloric acid. The mixture may be stirred for one hour and the solvent is thereafter dried under vacuum to provide n-acetyl beta alanine.

The reaction proceeds as follows: $CH_3COCl + 2HN-CH_2-CH_2-COOH \rightarrow Ch_3CONH-CH_2-CH_2-COOH + HCl$ Additional pharmaceutically acceptable additives or inert ingredients can also be added, and then the pharmaceutical composition can be separated into discrete quantities for distribution and/or administration.

Measuring specific quantities of N-acetyl beta alanine, water or solvent, and pharmaceutically acceptable additives or inert ingredients, may involve any number of steps and implementing components, and measuring specific quantities of N-acetyl beta alanine, water or solvent, and pharmaceutically acceptable additives or inert ingredients, may be accomplished readily from this disclosure. For the exemplary purposes of this disclosure, measuring specific quantities of N-acetyl beta alanine, water or solvent, and pharmaceutically acceptable additives or inert ingredients, may comprise using a scale, a solid or liquid dispensing apparatus, or other measurement device capable of measuring solid mass or liquid volume to produce a desired quantity of N-acetyl beta alanine, water or solvent, and pharmaceutically acceptable ingredient.

It should be appreciated that any of the components of particular implementations of an N-acetyl beta alanine Compound or Composition may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion Compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of N-acetyl beta alanine, water or solvent, and pharmaceutically acceptable additives or inert ingredients for Compounds, or mixing the measured quantities of N-acetyl beta alanine, and pharmaceutically acceptable additives or inert ingredients for Compositions, may involve any number of steps and implementing components, and may be accomplished readily from this disclosure.

For the exemplary purposes of this disclosure, mixing the measured quantities of N-acetyl beta alanine, water or solvent, and pharmaceutically acceptable additives or inert ingredients, may comprise combining the measured quantities of m N-acetyl beta alanine, water or solvent, and pharmaceutically acceptable additives or inert ingredients, under the influence of physical, ultrasonic, or electrostatic forces to create a desired degree of intermingling and/or chemical reaction of the N-acetyl beta alanine, water or solvent and any pharmaceutically acceptable ingredients. The mixed may be accomplished when the N-acetyl beta alanine, water or solvent and/or any pharmaceutically acceptable ingredients are in a solid, liquid, or semisolid state.

Separating the N-acetyl beta alanine Compound or Composition into discrete quantities for distribution may involve any number of steps and implementing components, and separating the N-acetyl beta alanine Compound or Composition into discrete quantities for distribution may be accomplished readily from this disclosure. For the exemplary purposes of this disclosure, separating the N-acetyl beta alanine Compound or Composition into discrete quantities for distribution may involve utilizing a specific piece of equipment, for example, a conventional tablet forming apparatus to shape the formed composition into individual tablets, each containing a desired dose of N-acetyl beta alanine Compound or Composition. The separating process may be accomplished when the N-acetyl beta alanine Compound or Composition is in a solid, liquid, or semisolid state.

Those of ordinary skill in the art will be able to readily select manufacturing equipment and pharmaceutically acceptable additives or inert ingredients to manufacture implementations of an N-acetyl beta alanine Compound or Composition. For the exemplary purposes of this disclosure, some examples of pharmaceutically acceptable additives or inert ingredients and manufacturing process are included below, particularly those that relate to manufacture of implementations of an N-acetyl beta alanine Compound or Composition in tablet form. Notwithstanding the specific examples given, it will be understood that those of ordinary skill in the art will readily appreciate how to manufacture implementations of an N-acetyl beta alanine Compound or Composition according to the other methods of administration and delivery disclosed in this document.

Accordingly, compounds and Compositions may include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

For example, a particular implementation of an N-acetyl beta alanine Compound or Composition may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of an N-acetyl beta alanine Compound or Composition may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of an N-acetyl beta alanine Compound or Composition to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of an N-acetyl beta alanine Compound or Composition may include diluents, or any inert substances added to increase the bulk of the N-acetyl beta alanine Compound to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in an N-acetyl beta alanine Compound or Composition and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

With respect to delivery of particular implementations of an N-acetyl beta alanine Compound or Composition, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. They are divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of an N-acetyl beta alanine composition or compound have been described in particular sequences of steps and/or in particular forms, it will be understood that such manufacture is not limited to the specific order of steps or forms as disclosed. Any steps or sequences of steps of manufacture of implementations of an N-acetyl beta alanine composition or compound in any form are given as examples of possible steps or sequences of steps or potential forms and not as limitations, since many possible manufacturing processes and sequences of steps may be used to manufacture N-acetyl beta alanine composition or compound implementations in a wide variety of forms.

Use

Implementations of an N-acetyl beta alanine Compound or Composition are particularly useful as supplements to increase athletic/sports/muscle performance in humans and animals, however, it can be used for any other use. However, implementations are not limited to these uses. Rather, any description relating to the foregoing is for the exemplary purposes of this disclosure. It will be understood that implementations of an N-acetyl beta alanine Compound or Composition may encompass a variety of uses for which beta-alanine is typically administered, such as muscle and overall health, anti-aging, nervous system health, etc.

Thus, in one aspect, a method is disclosed for enhancing athletic performance. The method includes administering a pharmaceutically effective amount to a human or animal of n-acetyl beta alanine.

In another aspect, a method is disclosed for preventing paresthesia. The method includes administering a pharmaceutically effective amount to a human or animal of n-acetyl beta alanine.

The N-acetyl form of beta alanine cannot react with nerve ends to produce paresthesia since amides are neurologically inactive. Therefore, by slowly converting to beta-alanine through deacetylation, paresthesia is prevented due to low but constant blood-serum beta alanine concentrations. This also increases the half-life of beta-alanine present in the blood stream and cell membrane permeability.

For the exemplary purposes of this disclosure, the Applicants have administered N-acetyl beta alanine to over 30 different subjects in doses ranging from 1 to even 10 grams. No paresthesia or negative feelings were described by any of the users. The paresthesia-preventing property of N-acetyl beta alanine is easy to prove—anyone can try to ingest 5 grams of beta-alanine and after the paresthesia has subsided consume 5 grams of n-acetyl-beta alanine and observe that no paresthesia takes place.

For the exemplary purposes of this disclosure, the Applicants have also administered N-acetyl-beta alanine at a dose of 5 grams per day ×1 in 10 subjects, all of them well trained athletes that had in the past used beta alanine and were well aware of it's benefits. All of the subjects had not used beta alanine for at least a month. They were asked to report the effects of the "new beta alanine preparation" they were offered. They all reported that N-acetyl-beta alanine resulted in improved effectiveness over normal beta-alanine and also that the full benefits were exhibited at a faster rate.

Based on these initial studies, the Applicants have moved forward with a major University to organize a study that will compare N-acetyl beta-alanine's effectiveness over beta-alanine's effectiveness.

As additional support, studies showing effectiveness for muscle performance and the like are as follows.

In "Role of beta-alanine supplementation on muscle carnosine and exercise performance", Artioli et al., Med Sci Sports Exerc. 2010 June; 42(6):1162-73, studies on beta alanine supplementation and exercise performance have demonstrated improvements in performance during multiple bouts of high-intensity exercise and in single bouts of exercise lasting more than 60 s. Similarly, beta alanine supplementation has been shown to delay the onset of neuromuscular fatigue. Although beta alanine does not improve maximal strength or VO2max, some aspects of endurance performance, such as anaerobic threshold and time to exhaustion, can be enhanced. Symptoms of paresthesia may be observed if a single dose higher than 800 mg is ingested.

In "Muscle carnosine metabolism and beta-alanine supplementation in relation to exercise and training", Derave et al., Sports Med. 2010 Mar. 1; 40(3):247-63 it explains that beta alanine is rapidly developing as a popular ergogenic nutritional supplement for athletes worldwide, and the currently available scientific literature suggests that its use is evidence based. However, many aspects of the supplement, such as the potential side effects and the mechanism of action, require additional and thorough investigation by the sports science community.

In "Beta-alanine supplementation reduces acidosis but not oxygen uptake response during high-intensity cycling exercise", Baguet et al., Eur J Appl Physiol. 2010 February; 108(3):495-503, results indicate that chronic beta-alanine supplementation, which presumably increased muscle carnosine content, can attenuate the fall in blood pH during high-intensity exercise. This may contribute to the ergogenic effect of the supplement found in some exercise modes.

In "Effect of beta-alanine supplementation on the onset of blood lactate accumulation (OBLA) during treadmill running: Pre/post 2 treatment experimental design", Jordan et al., Journal of the International Society of Sports Nutrition 2010, 7:20, it was demonstrated that beta alanine supplementation for 28 days enhanced sub-maximal endurance performance by delaying OBLA. However, βA supplemented individuals had a reduced aerobic capacity as evidenced by the decrease in $VO_{2max}$ values post supplementation.

In "Beta-alanine and the hormonal response to exercise", Hoffman et al., Int J Sports Med. 2008 December; 29(12): 952-8, results indicate that four weeks of beta alanine supplementation can significantly improve muscular endurance during resistance training in experienced resistance-trained athletes. However, these performance gains did not affect the acute endocrine response to the exercise stimulus.

In "The effects of 10 weeks of resistance training combined with beta-alanine supplementation on whole body strength, force production, muscular endurance and body composition", Kendrick et al., Amino Acids. 2008 May; 34(4):547-54, subjects were assessed prior to and after training for whole body strength, isokinetic force production, muscular endurance, and body composition. Beta alanine supplemented subjects increased Muscle-Carnosine by 12.81+/−7.97 mmol×kg(−1) dry muscle whilst there was no change in Placebo Group subjects.

As further support, one study showing effectiveness for mood improvement through dopamine increase and anxiolytic effects and the like is "The impact of taurine- and beta-alanine-supplemented diets on behavioral and neurochemical parameters in mice: antidepressant versus anxiolytic-like effects", Murakami et al., Amino Acids. 2010 July; 39(2):427-34, where results suggest that taurine-supplemented diet had an antidepressant-like effect and beta-alanine-supplemented diet had an anxiolytic-like effect.

As even further support, studies showing effectiveness for Antiaging/Geriatric effects and the like are the following:

In "The effect of beta-alanine supplementation on neuromuscular fatigue in elderly (55-92 Years): a double-blind randomized study", Stout et al., Journal of the International Society of Sports Nutrition 2008, 5:21, findings suggest that ninety days of beta alanine supplementation may increase physical working capacity by delaying the onset of neuromuscular fatigue in elderly men and women.

In "Carnosine and Its Possible Roles in Nutrition and Health", Hipkiss, Advances in Food and Nutrition Research, Volume 57, 2009, Pages 87-154, evidence for carnosine's possible protective action against secondary diabetic complications, neurodegeneration, cancer, and other age-related pathologies is briefly discussed.

In "Possible new antiaging strategies related to neuroendocrine-immune interactions", Mocchegiani et al., Neuroimmunomodulation. 2008; 15(4-6):344-50, discloses some substances which can be proposed as new antiaging strategies because of their capacity to remodel some biological functions in old animals and humans. Among them is carnosine It's role as possible antiaging strategy in healthy people in relation to neuroendocrine-immune responses and zinc ion bioavailability is reported and discussed.

In "Carnosine, the anti-ageing, anti-oxidant dipeptide, may react with protein carbonyl groups" Hipkiss, Mechanisms of Ageing and Development, Volume 122, Issue 13, 15 Sep. 2001, Pages 1431-1445, a preliminary experiment suggests that carnosine is effective in vivo; it suppressed diabetes-associated increase in blood pressure in fructose-fed rats, an observation consistent with carnosine's anti-glycating actions. Researchers speculate that: (i) carnosine's apparent anti-ageing actions result, partly, from its ability to react with carbonyl groups on glycated/oxidised proteins and other molecules; (ii) this reaction, termed 'carnosinylation,' inhibits cross-linking of glycoxidised proteins to normal macromolecules; and (iii) carnosinylation could affect the fate of glycoxidised polypeptides.

The invention claimed is:

1. A method for reducing muscle fatigue or increasing athletic performance in a human comprising, orally administering to the human 1 g to 10 g of N-Acetyl Beta Alanine as an alternative to beta alanine in order to prevent the onset of paresthesia in the human.

2. The method of claim 1, wherein absorption of beta alanine in the human is increased.

3. A method for increasing absorption of beta alanine in a human while preventing the onset of paresthesia, the method comprising orally administering to the human 1 g to 10 g of N-Acetyl Beta Alanine.

4. A method for preventing the onset of paresthesia in a human caused by beta alanine supplementation, the method comprising orally administering to the human 1 g to 10 g of N-Acetyl Beta Alanine as an alternative to beta alanine.

5. The method of claim 4, wherein absorption of beta alanine in the human is increased.

6. The method of claim 4, wherein muscle fatigue in the human is reduced.

7. The method of claim 4, wherein athletic performance of the human is increased.

\* \* \* \* \*